United States Patent [19]

Hess

[11] Patent Number: 5,573,526

[45] Date of Patent: Nov. 12, 1996

[54] SOFT SHELL RESERVOIR

[75] Inventor: Paul H. Hess, Plymouth, Minn.

[73] Assignee: Minntech Corporation, Minneapolis, Minn.

[21] Appl. No.: 436,827

[22] Filed: May 8, 1995

[51] Int. Cl.⁶ .................................................. A61B 19/00
[52] U.S. Cl. .............................. 604/408; 604/4; 604/122; 604/406; 604/122; 128/DIG. 3
[58] Field of Search .............................. 604/4, 5, 6, 122, 604/317, 403, 406, 408, 410; 422/44; 128/DIG. 3

[56] References Cited

U.S. PATENT DOCUMENTS

| 4,568,330 | 2/1986  | Kujawski et al. ........................ 604/4 |
| 4,622,032 | 11/1986 | Katsura et al. . |
| 4,643,713 | 2/1987  | Vitala . |
| 4,717,377 | 1/1988  | Fukasawa ................................ 604/4 |
| 4,734,269 | 3/1988  | Clarke et al. . |
| 4,863,452 | 9/1989  | Irmiter et al. . |
| 4,959,062 | 9/1990  | Gellman . |
| 4,976,707 | 12/1990 | Bodicky et al. ........................ 604/410 |
| 4,976,708 | 12/1990 | Oshiyama . |
| 5,061,236 | 10/1991 | Sutherland et al. . |
| 5,262,070 | 11/1993 | Ishida ...................................... 604/408 |
| 5,269,924 | 12/1993 | Rochat .................................... 604/410 |
| 5,318,556 | 6/1994  | Avallone et al. ........................ 604/403 |
| 5,352,218 | 10/1994 | Buckley et al. . |
| 5,484,431 | 1/1996  | Scharf et al. ............................ 604/408 |

FOREIGN PATENT DOCUMENTS

| 423841    | 4/1991  | European Pat. Off. ................ 604/408 |
| 404336076 | 11/1992 | Japan ...................................... 604/403 |

Primary Examiner—John G. Weiss
Assistant Examiner—Bruce E. Snow
Attorney, Agent, or Firm—Cushman Darby & Cushman, LLP

[57] ABSTRACT

A soft shell reservoir bag is provided as a storage reservoir for blood in a bypass extracorporeal circuit during open heart surgery. The reservoir bag is constructed to allow for the easy venting of air and to prevent the accidental delivery of air to patient. Blood enters the reservoir through the inlet port, passes through the microscreen and exits through the outlet port to a pump which feeds an oxygenator. The shape of the bag and component disposition give the bag its main advantages. The inlet port is positioned above the outlet port which puts a larger volume above the outlet port which promotes mixing and no vortex. Also the shape above the outlet port gives the bag a low hold-up volume and lower resistance to keep the bag open. The shape also promotes low venous resistance.

10 Claims, 2 Drawing Sheets

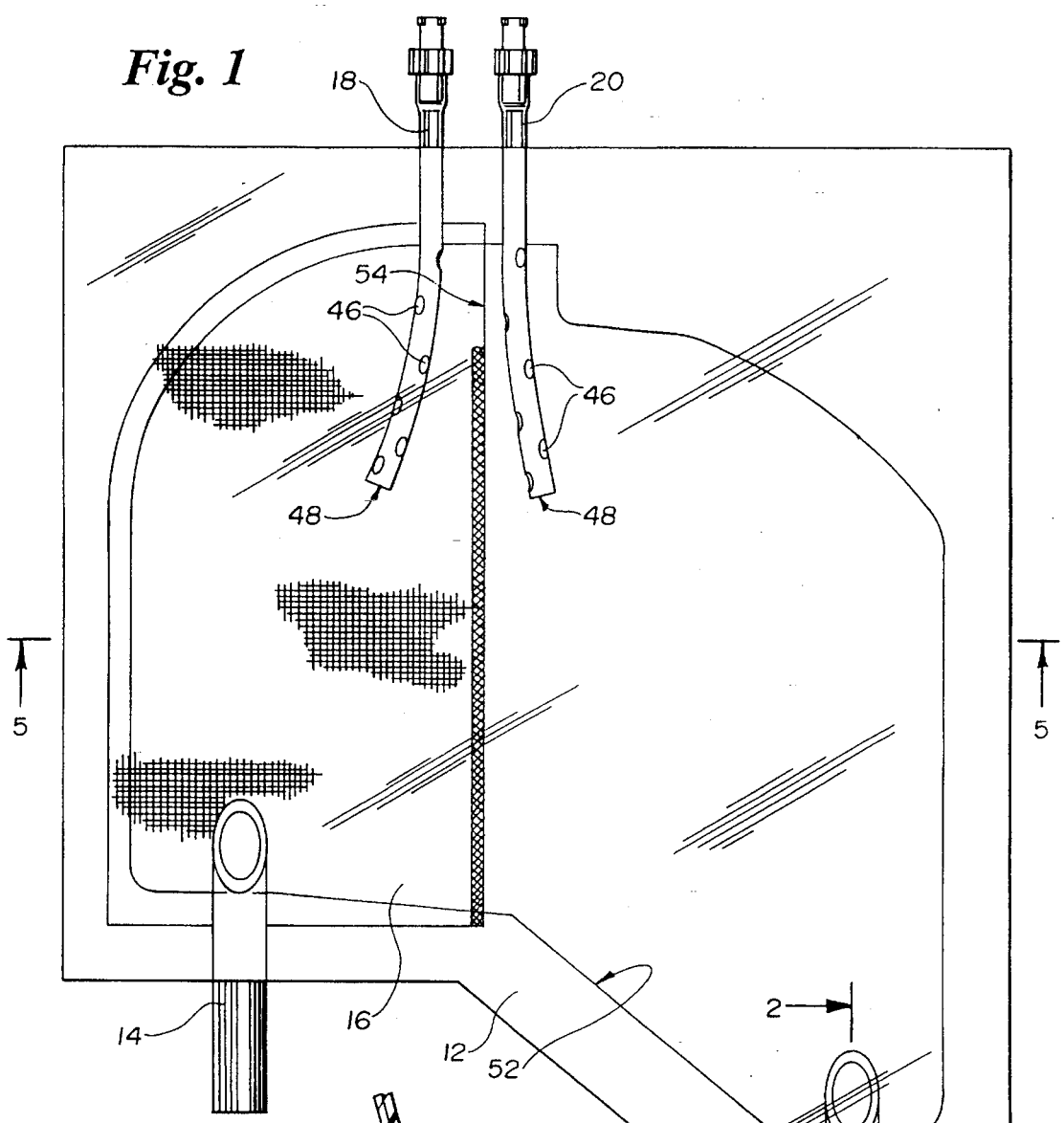
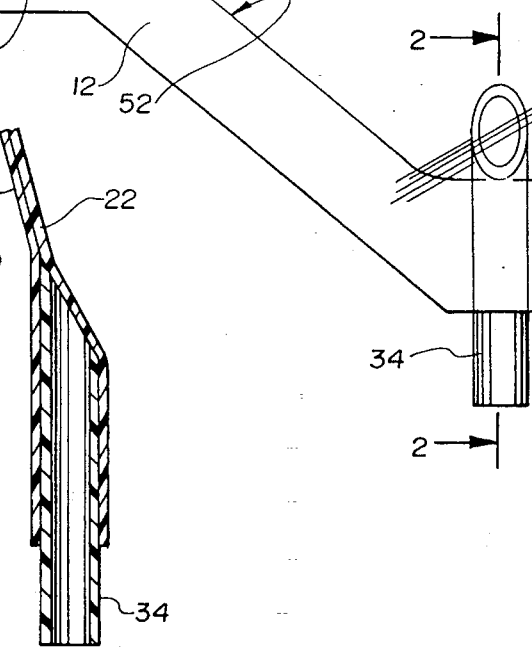

SOFT SHELL RESERVOIR

BACKGROUND OF THE INVENTION

1. Field of the Invention

The present invention relates to a venous reservoir bag and more particularly to a soft sided or soft shell reservoir that can hold a selectively variable amount of blood and which has a unique and advantageous shape.

2. Description of the Related Art

A venous reservoir bag is typically included in a cardiopulmonary bypass circuit to accommodate for variations in blood volume when cardiopulmonary bypass flow is connected through a membrane oxygenator and to separate the bubbles from the venous blood and to vent such separated gas to atmosphere. Conventional reservoir bags have a blood inlet and a blood outlet defined to extend into the bag from a bottom edge thereof and one or more air vents provided at the apex of the bag. When blood flows into the bag from the inlet and passes through the bag to the outlet, gas bubbles rise to the surface of the fluid in the reservoir and may be vented to atmosphere through the upper vent.

Prior art reservoirs of the type described above generally do not remove all gas bubbles from the blood, particularly if there is a low liquid volume in the bag and/or there are high blood flow rates through the reservoir.

SUMMARY OF THE INVENTION

It is an object of the present invention to provide a venous reservoir bag that maximizes gas bubble separation from the blood circulation line along which it is disposed. It is also an object of the invention to provide a venous reservoir having a unique shape that encourages flow without the generation of a vortex at the outlet, which might otherwise trap gas within the flowing blood.

The foregoing objects are realized in accordance with the invention by providing a soft shell reservoir bag as a storage reservoir for blood in a bypass extracorporeal circuit during open heart surgery. The reservoir bag is constructed to allow for the easy venting of air and to prevent the accidental delivery of air to patient. The reservoir receives blood directly from the patient and also from the cardiotomy reservoir. Blood enters the reservoir through the inlet port, passes through the microscreen and exits through the outlet port to a pump which feeds an oxygenator.

The advantages of the reservoir include: no vortex at the outlet, low holdup volume, and air retention for venting purposes. The shape of the bag gives the bag its main advantages. The inlet port positioned above the outlet port puts a larger volume above the outlet port which promotes mixing and no vortex. Also the shape above the outlet port gives the bag a low hold-up volume and lower resistance to keep the bag open. The shape also promotes low venous resistance.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 1 is a schematic elevational view of a soft sided reservoir provided in accordance with the invention;

FIG. 2 is a cross-sectional view taken along line 2—2 of FIG. 1 in the condition where the bag is collapsed;

DETAILED DESCRIPTION OF THE PRESENTLY PREFERRED EXEMPLARY EMBODIMENTS

Figure 3:
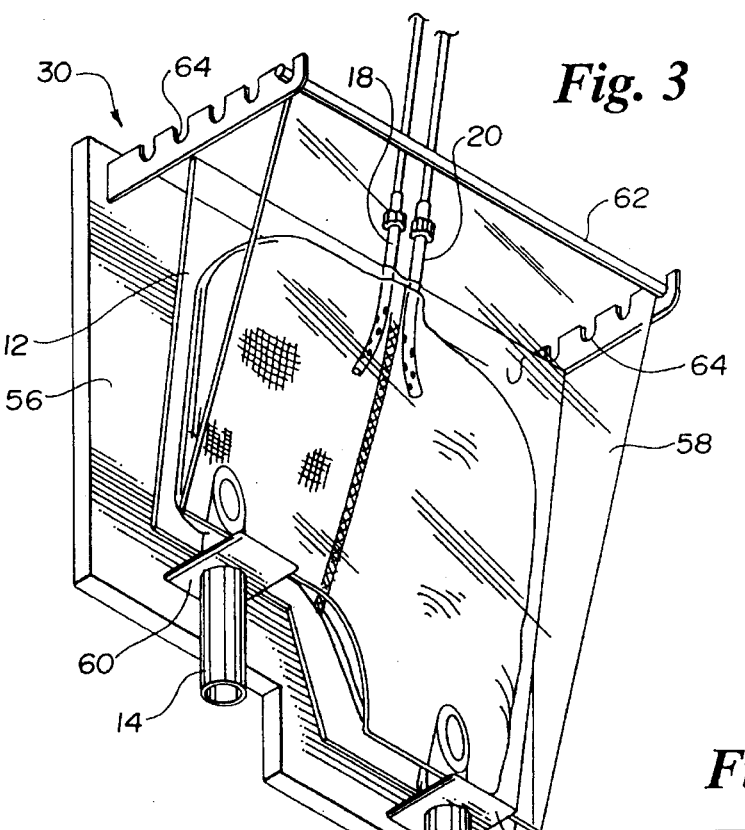
FIG. 3 is a perspective view from below of a blood reservoir holder provided in accordance with the present invention.
Figure 5:
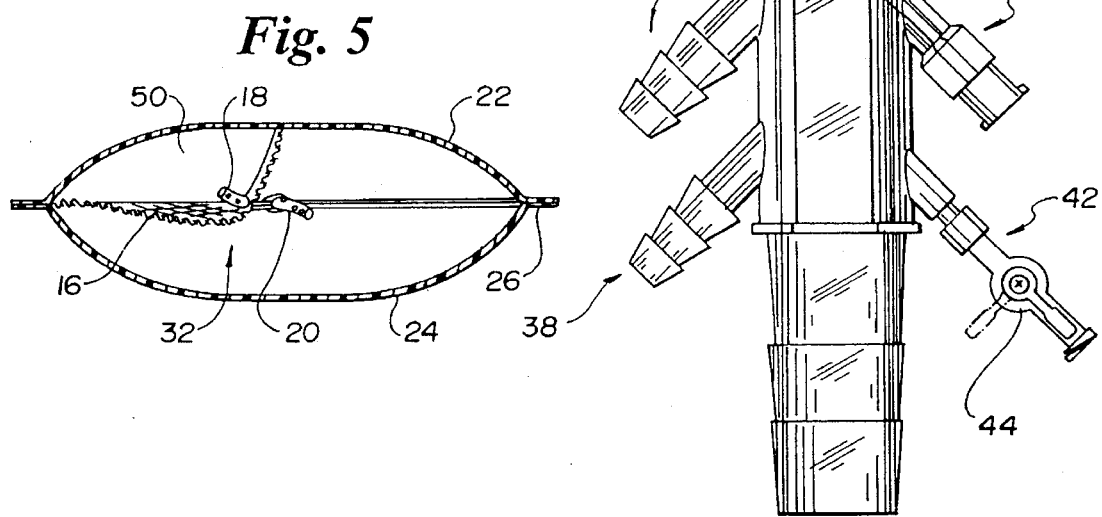
FIG. 5 is a schematic cross-sectional view taken along line 5—5 of FIG. 1 in which the reservoir is in its expanded blood containing configuration.

A soft sided liquid-gas separator provided in accordance with the present invention as shown by way of example in FIG. 1. The soft sided reservoir bag 10 comprises a container 12, an inlet tube 14, a filter element 16, and one or more access ports which may define vent tubes 18, 20, one extending into the interior of a filter compartment defined by the filter element, as detailed more particularly below, and the other extending into the remainder of the container.

The container 12 is in the form of a flexible, soft sided generally transparent bag which may be composed of first and second layers 22, 24 of a suitable biocompatible plastic material, such as PVC, which have been heat sealed along the peripheral edges thereof as at 26. As will be explained in greater detail below, in accordance with the present invention, the bag 10 is mounted to suitable supports (not shown) of a unique soft shell blood reservoir holder 30. To facilitate mounting of the bag to the holder, one or more tear resistant strips may be incorporated in the heat sealed perimeter of the container, between the layers of the bag and having openings by which the reservoir can be suspended within the holder.

The plastic material for defining the container 12, as noted above, is heat sealed about the periphery of the plastic layers so as to define a blood receiving compartment 32. In flow communication with the interior compartment of the container is a blood inlet 14 and a blood outlet 34, each of which are bonded to the material of the container during the heat sealing process. The inlet and outlet tubes are relatively rigid so that even when the container is collapsed the inlet and outlet tubes are not collapsed, as shown in FIG. 2. In the illustrated embodiment, the inlet tube 14 is a ½ inch inner diameter ("ID") tube and the outlet tube 34 is a ⅜ inch ID tube.

Figure 4:
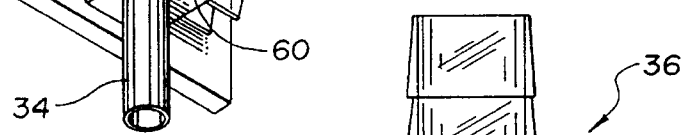
FIG. 4 is a schematic elevational view of a blood line access station which may be selectively disposed at the blood inlet to permit sampling and/or testing of blood flowing into the reservoir.

A blood line access station 36, as illustrated for example in FIG. 4 and which may be coupled to the inlet port 14, includes a ⅜ inch cardiotomy port 37, a ¼ inch recirculation port 38, IV access ports 38, a thermometer or other temperature sensing port 40 and a sample port 42 having a conventional stop cock valve 44. As an alternative, one or more access stations may be provided, each having a subset of the port structures shown in FIG. 4, as deemed necessary or desirable. Thus, for example, two access stations could be provided, one having the ports shown on the left in FIG. 4 and the other having the ports shown on the right in FIG. 4.

The access or air vent tubes 18, 20 extend through the heat sealed periphery of the container at the apex of the blood receiving compartment or non-bonded reservoir portion of the shell. The air vent tubes may be bonded to the shell during the heat sealing process or otherwise secured with respect thereto in fluid tight relation. The air vents are preferably perforated as at 46 interiorly of the bag in addition to having an axial opening 48 at the lowermost extent thereof. This ensures the free passage of air to be vented from the container in spite of the presence of fluid within the bag and the potential for the bag to collapse against a portion of the tube. Indeed, providing a plurality of perforations in the tubes ensures that any bag collapse will not necessarily obstruct passage of air from the bag.

A filter element 16 is mounted within the non-bonded portion of the shell. More particularly, the filter, hereinafter referred to as microscreen, is bonded to one layer of the container along a mid line portion, but not necessarily the width-wise center, of that layer. Indeed, it is envisioned that a microscreen which extends approximately one-quarter to one-half across the width of the bag will be sufficient for the purposes of the invention. The microscreen is also bonded to one or both layers of the bag at a region spaced from the mid line portion of the one layer so that the microscreen defines an upstream filter compartment 50 with the one layer. The microscreen is bonded to the layer(s) so that the blood inlet opens into the upstream filter compartment 50. By way of example, it is currently preferred that the microscreen be bonded to the front layer 22 to define compartment 50 and that the front layer with microscreen bonded thereto then be bonded to the rear layer 24. The microscreen is free from bonding to the front and rear layers adjacent the apex of the reservoir to permit blood overflow in the event the microscreen becomes clogged or otherwise obstructs flow.

In the illustrated and presently preferred embodiment, the microscreen is a polyester microscreen having a pore diameter of approximately 50–250 microns, and currently most preferably about 105 microns. The microscreen is intended to separate gas bubbles such as air bubbles from the blood but not otherwise filter or separate the blood.

As can be seen in particular in FIG. 1, the layers defining the container or blood reservoir are heat sealed together so as to define a non-bonded reservoir portion of asymmetric configuration. Indeed, the non-bonded reservoir portion of the shell defines an inclined bottom wall 52 adjacent the blood outlet 34 so as to channel and direct blood therewithin towards the outlet thereby providing a reservoir having a low hold up volume. Further, the reservoir as so constructed and arranged provides a blood inlet 14 which is disposed above the blood outlet 34.

In use, the reservoir bag is connected in line as a part of an extracorporeal circuit during cardiopulmonary bypass surgery. When provided in such a circuit, the soft shell reservoir bag receives blood from a patient through the inlet tube. The inlet tube directs the incoming blood into the filter compartment 50. As such, blood flow within the container is generally towards the air vent 18 and gas bubbles within the blood will tend to pass towards that vent and be vented to atmosphere. The microscreen 16 permits blood to pass therethrough but inhibits the passage of gas bubbles which further tends to separate the gas bubbles from the blood and allow the gas to pass upwardly to the apex of the container and out through one or the other of the vents 18, 20.

The blood that passes through the microscreen then flows towards the outlet 34. The shape of the container adjacent the outlet defines a pool for the blood to temporarily collect which further permits gas bubbles to separate and pass upwardly from the blood and towards the vent 20. In the event the microscreen becomes clogged so that blood cannot pass therethrough rapidly enough to keep pace with incoming blood flow, the blood can flow through the gap 54 at the apex of the container so that blood will continue to the outlet. Moreover, even if the reservoir is filled to that level, the perforations in the air vent tubes permit gas to be vented from the reservoir.

To suspend the soft shell reservoir of the invention and to control the total volume thereof, a soft shell holder 30 is further provided in accordance with the invention. The soft shell reservoir holder 30 includes a base plate 56 which may be suitably supported relative to the remainder of the extra corporeal system, for example, on an IV pole or other support structure. A volume restriction plate 58 is mounted to define a preferably V-shaped gap of select size with the base plate 56. Thus, the reservoir can hold a predetermined, variable volume of blood depending on how the restriction plate is positioned. Both the base plate and the restriction plate may be formed from any suitable material but for cost and weight considerations are preferably separately formed from acrylic. Two or more pins, for example, (not shown) may be provided to project from the base plate, spaced apart and disposed so as to be selectively aligned with corresponding holes (not shown) defined in the upper bonded portion of the shell such that the reservoir can be suspended from the base plate.

The blood reservoir holder 30 provided in accordance with the invention may include, for example, restriction plate retainer clips 60 for receiving the blood inlet 14 and filtered blood outlet 34 tubes. In the illustrated embodiment, the restriction plate retainer clips are projecting tabs having a circular orifice through which the inlet and outlets tubes may be telescopically received before coupling to suitable tubing. An alternative to the illustrated structure would be, for example, a substantially U-shaped tab defining a slot for receiving the blood inlet tube and the blood outlet tube, respectively. To pivotally mount the front plexiglass or acrylic volume restriction plate, the restriction plate retainer clips may be provided with a suitable hinge structure or a series of transverse grooves defining seats for the bottom edge of the restriction plate.

More particularly, in the illustrated embodiment, the reservoir volume is adjusted by varying the angle defined by the volume restriction plate and the base plate. The volume restriction plate 58 may thus have an adjustment rod structure 62 provided at an upper edge thereof which is selectively seated in one of several pairs of adjustment slots 64. In the event the volume restriction plate is hingedly coupled to the retainer clips, the hinge structure provided must be suitably mounted or flexible so as to allow the restriction plate to be selectively lifted for the adjustment rod to be disposed selectively in one of the pairs of adjustment slots. In the alternative, in the event transverse grooves are provided in the retainer clips the volume restriction plate can be selectively seated in the groove following proper placement of the adjustment rod in the adjustment slots. As yet a further alternative, the restriction plate retaining clips may be mounted so as to be inclined upwardly relatively to the base plate to define a receiving pocket or slot for the restriction plate at the apex of the retainer clip and the inlet and outlet tubes.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. A soft shell reservoir comprising:

first and second flexible layers secured together about a periphery thereof to define a container having a fluid receiving compartment defined therewithin, said first and second layers respectively defining front and rear walls of said container;

an inlet port and an outlet port operatively coupled to said container, a fluid flow path being defined through said fluid receiving compartment to extend from the inlet port to the outlet port;

a microscreen element mounted so as to extend across at least a portion of said fluid receiving compartment, said microscreen element intersecting said flow path, thereby to define an upstream, filter compartment and a downstream compartment, said upstream compartment being disposed between said inlet and said microscreen element and said downstream compartment being disposed between said microscreen element and said outlet, said microscreen permitting liquid to pass therethrough but inhibiting passage of gas bubbles, said inlet being in flow communication with said upstream compartment, said filter element being positioned and arranged within said container so as to define a bypass flow passage around said microscreen element at a vertically upper portion of said upstream compartment leading into a vertically upper portion of said downstream compartment; and at least one vent tube operatively coupled to a vertically upper portion of said container.

2. A reservoir as in claim 1, wherein there are two vent tubes, one of said vent tubes extending into said vertically upper portion of said upstream compartment and the other of said vent tubes extending into said vertically upper portion of said downstream compartment.

3. A reservoir as in claim 1, wherein each said vent tube is perforated so as to have a plurality of radial openings.

4. A reservoir as in claim 1, wherein in said inlet port opens into said upstream compartment at a level vertically higher than a level at which said outlet port opens into said downstream compartment.

5. A reservoir as in claim 4, wherein a bottom peripheral edge of said fluid receiving compartment is inclined generally downwardly from a vertical level of said inlet port towards a vertical level of said outlet port, whereby a low hold up volume region is defined adjacent said outlet port.

6. A reservoir as in claim 1, wherein at least one of said inlet port and said outlet port are operatively coupled to said container so that a longitudinal axis of said at least one port is oriented generally vertically.

7. A soft shell reservoir in combination with a volume restricting holder assembly, said reservoir comprising:

first and second flexible layers secured together about a periphery thereof to define a container having a fluid receiving compartment defined therewithin, said first and second layers respectively defining front and rear walls of said container;

an inlet port and an outlet port operatively coupled to said container, a fluid flow path being defined through said fluid receiving compartment to extend from the inlet port to the outlet port;

a microscreen element mounted so as to extend across at least a portion of said fluid receiving compartment, said microscreen element intersecting said flow path, thereby to define an upstream, filter compartment and a downstream compartment, said upstream compartment being disposed between said inlet and said microscreen element and said downstream compartment being disposed between said microscreen element and said outlet, said microscreen permitting liquid to pass therethrough but inhibiting passage of gas bubbles, said inlet being in flow communication with said upstream compartment, said filter element being positioned and arranged within said container so as to define a bypass flow passage around said microscreen element at a vertically upper portion of said upstream compartment leading into a vertically upper portion of said downstream compartment; and at least one vent tube operatively coupled to a vertically upper portion of said container; and said volume restricting holder assembly comprising:

a relatively rigid base plate and a volume restriction plate mounted so as to define a generally V-shaped gap of variable size with said base plate, said holder assembly being adapted to receive said reservoir in said V-shaped gap between said restriction plate and said base plate, thereby to limit the volume of said fluid receiving compartment.

8. A reservoir as in claim 7, wherein said V-shaped gap can be selectively varied to selectively determine the volume of said fluid receiving compartment of said reservoir mounted thereto.

9. The combination of claim 8, wherein said volume can be selectively determined to be one of a plurality of volumes, greater than a minimum volume of said fluid receiving compartment and less than a maximum volume of said fluid receiving compartment.

10. A soft shell reservoir comprising:

first and second flexible layers secured together about a periphery thereof to define a container having a fluid receiving compartment defined therewithin, said first and second layers respectively defining front and rear walls of said container;

an inlet port and an outlet port operatively coupled to said container, a fluid flow path being defined through said fluid receiving compartment to extend from the inlet port to the outlet port, said inlet port opening into said fluid receiving compartment at an area laterally spaced from and vertically higher than an area of said fluid receiving compartment into which said outlet port opens, a bottom peripheral edge of said fluid receiving compartment being inclined generally downwardly from a vertical level of said inlet port toward a vertical level of said outlet port intermediate said inlet and outlet ports, thereby to define a low hold up volume region adjacent said outlet port;

a vent tube operatively coupled to a vertically upper portion of said container; and a microscreen element mounted so as to extend across at least a portion of said fluid receiving compartment, said microscreen element intersecting said flow path, thereby to define an upstream, filter compartment and a downstream compartment, said upstream compartment being disposed between said inlet and said microscreen element and said downstream compartment being disposed between said microscreen element and said outlet, said microscreen permitting liquid to pass therethrough but inhibiting passage of gas bubbles, said inlet being in flow communication with said upstream compartment wherein said filter element is positioned and arranged within said container so as to define a bypass flow passage around said microscreen element at a vertically upper portion of said upstream compartment leading into a vertically upper portion of said downstream compartment.

* * * * *